United States Patent [19]

Rambach

[11] Patent Number: 5,716,799
[45] Date of Patent: Feb. 10, 1998

[54] METHOD FOR THE IDENTIFICATION OF MICROORGANISMS WITH A CARBOHYDRATE-SUPPLEMENTED MEDIUM

[76] Inventor: Alain Rambach, 73 boulevard Montparnasse, 75006 Paris, France

[21] Appl. No.: 591,531

[22] PCT Filed: Jul. 28, 1994

[86] PCT No.: PCT/FR94/00957

§ 371 Date: Jan. 26, 1996

§ 102(e) Date: Jan. 26, 1996

[87] PCT Pub. No.: WO95/04156

PCT Pub. Date: Feb. 9, 1995

[30] Foreign Application Priority Data

Jul. 28, 1993 [FR] France ................. 93 109293

[51] Int. Cl.⁶ ............................................. C12Q 1/04
[52] U.S. Cl. ............................................. 435/34; 435/29
[58] Field of Search .................... 435/4, 7.2, 29, 435/30, 34

[56] References Cited

U.S. PATENT DOCUMENTS

| | | | |
|---|---|---|---|
| 4,874,695 | 10/1989 | Pincus | 435/19 |
| 4,892,817 | 1/1990 | Pawlak | 435/21 |
| 5,210,022 | 5/1993 | Roth et al. | 435/34 |
| 5,330,889 | 7/1994 | Monget | 435/34 |
| 5,358,854 | 10/1994 | Ferguson | 435/14 |
| 5,364,767 | 11/1994 | Flowers et al. | 435/39 |
| 5,393,662 | 2/1995 | Roth et al. | 435/38 |
| 5,449,612 | 9/1995 | Lepargneur et al. | 435/18 |
| 5,464,755 | 11/1995 | Bochner | 435/34 |
| 5,510,243 | 4/1996 | Boyd et al. | 435/18 |
| 5,534,415 | 7/1996 | Orenga | 435/34 |

FOREIGN PATENT DOCUMENTS

| | | |
|---|---|---|
| 0065137 | 11/1982 | European Pat. Off. . |
| 2684110 | 5/1993 | France . |
| 2717978 | 11/1977 | Germany . |
| 9012888 | 11/1990 | WIPO . |
| 9212259 | 7/1992 | WIPO . |

Primary Examiner—John Kight
Assistant Examiner—Dameron Jones

[57] ABSTRACT

A method for revealing the presence or absence of a particular microorganism strain in a medium, wherein at least one strain enzyme substrate chromogen and at least one compound selected from a high-concentration carbohydrate are added to the culture medium so that a derived colour differing from the basic colour of the chromophore is obtained once the chromogen has been hydrolysed.

14 Claims, No Drawings

METHOD FOR THE IDENTIFICATION OF MICROORGANISMS WITH A CARBOHYDRATE-SUPPLEMENTED MEDIUM

The present invention relates to a method for demonstrating the presence or absence of a particular strain of microorganism in a culture medium.

The detection of microorganism [sic] is very important, in particular in the food industry, in relation to water monitoring or in medicine, in view of the fact that these microorganisms may not only prove to be pathogenic agents, but can also consist of agents that reveal some types of contamination.

Various methods enable the presence of microorganisms in a medium of some kind to be demonstrated, consisting in taking a sample of the medium in question and then in promoting the growth of the microorganisms present by culture on or in a suitable medium.

In order to simplify the demonstration of the microorganisms present, the use has been proposed, in the detection medium, of colored compounds whose presence is characteristic of a given microorganism.

The coloration often reveals an enzyme activity associated with the microorganism in question, and the outcome of this activity may result in a modification of the pH of the medium, revealed by a colored indicator (EP-A-0 395 532), or alternatively in the liberation of a chromophoric or fluorophoric compound (FR-A-2-684,110).

Chromophores or fluorophores are compounds generally obtained by enzymatic hydrolysis of corresponding chromogenic or fluorogenic compounds present in the culture medium.

Fluorophores emit a characteristic radiation by fluorescence.

Chromophoric compounds are characterized by a color with a dominant wavelength.

Among known chromophoric compounds, indoxyl derivatives, hydroquinoline [sic] or alternatively naphthoic derivatives, or naphthyl and phenyl derivatives, may be noted in particular.

In order to differentiate two different genera of microorganisms in a culture medium, the proposal has even been made to introduce two chromogenic agents each liberating a chromophoric compound with a color characteristic of the presence of a particular microorganism (U.S. Pat. No. 5,210,022).

Although all of these media are efficacious in detecting microorganisms of a specific genus, such as, for example, Salmonella, Candida or *E. coli*, and distinguishing them from other species, they do not, however, permit the detection of a large number of microorganisms of different genera on the same culture medium, or the differentiation of pathogenic species from others among microorganisms of the same genus.

Such a distinction appears to be all the more important for certain species of yeasts, such as *Candida albicans* which is responsible for more than 50% of pathologies associated with yeasts.

In point of fact, it was unexpectedly found that these drawbacks could be remedied by introducing into the culture medium at least one chromogen which is a substrate for an enzyme of the strain and at least one compound chosen from a carbohydrate at high concentration, so as to obtain a derived color different from the basic color of the chromophore.

Derived color is understood to mean any color whose dominant wavelength differs from the dominant wavelength of the chromophores liberated by the chromogens present in the culture medium, taken separately in a standard medium.

Standard medium is understood to mean any ordinary identification medium in which the carbohydrate has a simple function of carbon source, at very low or even zero concentrations, where it is considered that such concentrations make it possible to avoid any inducing effect which would modify the behavior of the microorganisms in an uncontrolled manner and would induce errors in the identification of the microorganisms in question.

The dominant wavelength of the chromophore may be calculated by reference to daylight, as defined by the CIE (International Commission on Energy [sic]) as illuminant $D_{65}$, using any standard method for measuring the color of an object, especially with a spectrocolorimeter.

Hence the present invention relates to a method for demonstrating the presence or absence of a particular strain of microorganism in a medium, characterized in that at least one chromogen which is a substrate for an enzyme of the strain and at least one compound chosen from a carbohydrate at high concentration are introduced into the culture medium, so as to obtain after hydrolysis of the chromogen a color different from the basic color of the chromophore.

The medium is advantageously a peptone-based medium.

Carbohydrate is understood according to the invention to mean all sugars, natural or otherwise, especially monosaccharides, in particular pentoses or hexoses, preferably glucose.

The high carbohydrate concentration is of the order of 10 to 30 g/l of medium.

Moreover it was also found that the addition of a phosphate at high concentration, when one of the enzymes is phosphatase, enabled the number of derived colors capable of being obtained by the method according to the invention to be increased.

Consequently, the present invention relates to a method as defined above in which the culture medium comprises a high phosphate concentration, preferably of between 1 and 3 g/l.

The chromogens are, in particular, substrates for the following enzymes: β-galactosidase, β-glucuronidase, β-glucosidase, α-glucosidase, α-galactosidase, phosphatase, N-acetyl-β-gluconidase, N-acetyl-β-galactosidase, α-mannosidase, sulfatase, esterase, lipase and peptidase.

The medium advantageously comprises at least two chromogens, especially ones chosen from compounds of the same chemical family, preferably from those which liberate on hydrolysis two different chromophores which can undergo a coupling reaction.

Coupling reaction is understood to mean any physicochemical interaction through which the resulting dominant wavelength is different from the dominant wavelength of the mixture of the two chromophores taken separately.

Preferably, the chromogens are of the indoxyl family, especially alkylated, halogenated or dihalogenated indoxyl derivatives.

Preferred chromophores derived from indoxyl include the indoxyl derivatives bromoindoxyl, chloroindoxyl, dichloroindoxyl, chlorobromoindoxyl, trichloroindoxyl and methylindoxyl, especially the following derivatives: 6-chloroindoxyl, 5-bromoindoxyl, 3-bromoindoxyl, 4,6-dichloroindoxyl, 6,7-dichloroindoxyl, 5-bromo-4-chloroindoxyl, 5-bromo-6-chloroindoxyl or 4,6,7-trichloroindoxyl.

Microorganism whose presence or absence is demonstrated by the method according to the invention is understood to mean yeasts, molds or unicellular fungi and bacteria.

The method according to the invention is especially suitable for demonstrating the presence or absence of yeasts of the genus Candida, especially *Candida albicans* and *Candida tropicalis*.

Similarly, the bacteria whose presence or absence is capable of being demonstrated by the method according to the invention include, in particular, bacteria of the genus Streptococcus, Klebsiella, Enterobacter, Escherichia, Citrobacter, Staphylococcus, Listeria, Clostridium or Proteus.

The examples below enable the method according to the invention to be illustrated without, however, seeking to limit its scope.

TABLE I

Examples of derived coloration [sic]

| Chromogen | Medium in g/l | |
|---|---|---|
| | Agar 15<br>NaCl 5<br>Peptone 5<br>Meat extract 1 | Agar 15<br>Peptone 10<br>Glucose 20 |
| 5-Bromo-4-chloro-3-indoxyl N-acetylgluco-saminide 0.100 | bluish | light green** |
| 5-Bromo-6-chloro-3-indoxyl N-acetylgluco-saminide 0.100 | reddish | light beige** |
| 5-Bromo-4-chloro-3-indoxyl phosphate 0.100 | bluish | light green** |
| 5-Bromo-6-chloro-3-indoxyl phosphate 0.100 | reddish | light beige** |
| 6-Chloro-3-indoxyl phosphate 0.200 | pinkish | whitish** |

**derived color

TABLE II

Examples of coloration according to the invention for miscellaneous species of yeast Culture media: the following media were prepared for carrying out the method according to the invention.

A(g/l): (comparative) agar (15), peptone (5), yeast extract (2), meat extract (1), NaCl (5), 5-bromo-4-chloro-3-indoxyl N-acetylglucos-aminide (0.1).

B(g/l): agar (15), peptone (10), glucose (20), 5-bromo-4-chloro-3-indoxyl-N-acetylglucosamine (0.1)

C (g/l): agar (15), peptone (5), glucose (20), phosphate (2), 5-bromo-4-chloro-3-indoxyl N-acetylgluco-saminide (0.1), 5-bromo-6-chloro-3-indoxyl phosphate (0.1).

| | A | B | C |
|---|---|---|---|
| Candida albicans | bluish | green** | blue-green** |
| Candida glabrata | colorless | colorless | violet-pink** |
| Candida guilliermondii | | | pale violet-pink** |
| Candida krusei | | | violet-pink** |
| Candida lusitaniae | | | pale violet-pink** |
| Candida parapsilosis | | | gray-white** |
| Candida tropicalis | bluish | bluish | metallic blue* (with halo) |
| Cryptococcus neoformans | | | pink-white** |
| Trichosporon beigelii | | | gray-pink** |

*accessory color,
**derived color

The above results show that the addition of glucose and phosphate makes it possible to broaden the range of colors available for the same medium, making it possible here to distinguish seven different species, and especially to identify *Candida albicans* unambiguously.

I claim:

1. A method for demonstrating the presence or absence of a particular strain of microorganism in a culture medium, comprising:

introducing at least one chromogen which is a substrate for an enzyme of the strain and at least one compound chosen from a carbohydrate at high concentration into the culture medium, so as to obtain, after hydrolysis of the chromogen, a derived color different from the basic color of the chromophore.

2. The method of claim 1, wherein the medium is a peptone-based medium.

3. The method of claim 1, wherein the carbohydrate concentration is of the order of 10 to 30 g/l.

4. The method of claim 1, wherein the medium comprises a high phosphate concentration.

5. The method of claim 4, wherein the phosphate concentration is between 1 and 3 g/l.

6. The method of claim 1, wherein the medium contains at least two chromogens.

7. The method of claim 6, wherein the chromogens are compounds of the same chemical family.

8. The method of claim 6, wherein the two chromogens liberate on hydrolysis two different chromophores which can undergo a coupling reaction.

9. The method of claim 7, wherein the chromogens are selected from the indoxyl family.

10. The method of claim 8, wherein the chromophore is chosen from the indoxyl derivatives bromoindoxyl, chloroindoxyl, dichloroindoxyl, chlorobromoindoxyl, trichloroindoxyl and methylindoxyl, and especially the following derivatives: 6-chloroindoxyl, 5-bromoindoxyl, 3-bromoindoxyl, 4,6-dichloroindoxyl, 6,7-dichloroindoxyl, 5-bromo-4-chloroindoxyl, 5-bromo-6-chloroindoxyl or 4,6,7-trichloroindoxyl.

11. The method of claim 1, wherein the microorganisms are yeasts.

12. The method of claim 10, wherein the yeasts are of the genus Candida.

13. The method of claim 1, wherein the microorganisms are bacteria.

14. The method of claim 13, wherein the bacteria are of the genus Streptococcus, Elebsiella, Enterobacter, Escherichia, Citrobacter, Staphylococcus, Listeria, Clostridium or Proteus.

* * * * *